US006776760B2

(12) United States Patent
Marmarelis

(10) Patent No.: US 6,776,760 B2
(45) Date of Patent: Aug. 17, 2004

(54) MULTI-MODE PROCESSING FOR ULTRASONIC IMAGING

(75) Inventor: Vasilis Z. Marmarelis, Irvine, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 0 days.

(21) Appl. No.: 10/382,235

(22) Filed: Mar. 5, 2003

(65) Prior Publication Data

US 2003/0171677 A1 Sep. 11, 2003

Related U.S. Application Data

(60) Provisional application No. 60/362,568, filed on Mar. 6, 2002.

(51) Int. Cl.[7] .................................................. A61B 8/02
(52) U.S. Cl. ...................................................... 600/448
(58) Field of Search ................................ 600/442, 449, 600/547, 372, 437, 425, 448; 378/62; 382/128, 130–132, 159–160, 173, 190–192, 195, 204, 266

(56) References Cited

U.S. PATENT DOCUMENTS

| | | | |
|---|---|---|---|
| 4,322,974 A | | 4/1982 | Abele et al. |
| 4,328,707 A | * | 5/1982 | Clement et al. .............. 73/618 |
| 4,509,368 A | * | 4/1985 | Whiting et al. ............... 73/624 |
| 4,688,428 A | | 8/1987 | Nicolas |
| 4,817,015 A | * | 3/1989 | Insana et al. ............... 600/437 |
| 4,855,911 A | * | 8/1989 | Lele et al. .................. 600/442 |
| 4,922,917 A | * | 5/1990 | Dory .......................... 600/437 |
| 4,945,478 A | * | 7/1990 | Merickel et al. ........... 382/131 |
| 4,982,339 A | * | 1/1991 | Insana et al. ............... 600/437 |
| 5,065,763 A | * | 11/1991 | Green et al. ................ 600/453 |
| 5,279,301 A | * | 1/1994 | Tsukaya et al. ............ 600/442 |
| 5,361,767 A | * | 11/1994 | Yukov ........................ 600/442 |
| 5,417,215 A | * | 5/1995 | Evans et al. ................ 600/442 |
| 5,501,224 A | | 3/1996 | Shiki |
| 5,602,891 A | * | 2/1997 | Pearlman .................... 378/62 |
| 5,628,322 A | | 5/1997 | Mine |
| 5,720,291 A | * | 2/1998 | Schwartz .................... 600/456 |
| 5,746,209 A | * | 5/1998 | Yost et al. .................. 600/453 |

(List continued on next page.)

OTHER PUBLICATIONS

Marmarelis, Vasilis Z. et al., "High Resolution Ultrasonic Transmission Tomography", SPIE International Symposium, Medical Imaging, Feb. 2003, San Diego, CA, USA.

Kim, Tae–Seong et al., "Multi–band Tissue Differentiation in Ultrasonic Transmission Tomography", SPIE International Symposium, Medical Imaging, Feb. 2003, San Diego, CA, USA.

Kim, Tae–Seong et al., "Nonlinear Modeling of Ultrasonic Transmit–Receive System Using Laguerre–Volterra Networks", SPIE International Symposium, Medical Imaging, Feb. 2003, San Diego, CA, USA.

Primary Examiner—Mary Beth Jones
Assistant Examiner—Ruby Jain
(74) Attorney, Agent, or Firm—McDermott Will & Emery LLP

(57) ABSTRACT

Systems and methods for obtaining images of body organs or other tissue for each of their multiple characterizing aspects, and for classifying different tissue types within the images according to their characterizing aspects, are disclosed herein. The tissue may be irradiated with an ultrasonic signal, and an interaction signal received in return. Sinogram data may be constructed from the received interaction signal, and multiple characterizing data extracted therefrom. The multiple characterizing data representing multiple characterizing aspects may then be matched to tissue type within a database containing information correlating characterizing multi-aspect data with tissue type. Images of the tissue may then be presented with identifiers associating tissue portions with their matched tissue types.

8 Claims, 3 Drawing Sheets

U.S. PATENT DOCUMENTS

| | | | | |
|---|---|---|---|---|
| 5,800,350 A | * | 9/1998 | Coppleson et al. | 600/372 |
| 5,810,742 A | * | 9/1998 | Pearlman | 600/547 |
| 6,007,489 A | * | 12/1999 | Yost et al. | 600/449 |
| 6,120,445 A | * | 9/2000 | Grunwald | 600/437 |
| 6,138,045 A | * | 10/2000 | Kupinski et al. | 600/425 |
| 6,287,259 B1 | * | 9/2001 | Grunwald | 600/437 |
| 6,385,474 B1 | * | 5/2002 | Rather et al. | 600/407 |
| 6,415,046 B1 | * | 7/2002 | Kerut, Sr. | 382/128 |
| 6,468,215 B1 | * | 10/2002 | Sarvazyan et al. | 600/438 |
| 6,475,150 B2 | | 11/2002 | Haddad | |
| 6,514,202 B2 | * | 2/2003 | Grunwald | 600/437 |

* cited by examiner

MULTI-MODE PROCESSING FOR ULTRASONIC IMAGING

CROSS REFERENCE TO RELATED APPLICATION

This application is related to and claims the benefit of the filing date of U.S. provisional application Serial No. 60/362,568, filed Mar. 6, 2002, entitled "Multi-Mode Processing for Ultrasonic Imaging," the contents of which are incorporated herein by reference.

BACKGROUND OF THE INVENTION

1. Field of the Invention

The invention relates to imaging of body organs and tissues. The invention also relates to systems and methods for classifying tissue types.

2. General Background and State of the Art

Ultrasound has been a popular medical imaging technique for many years. Ultrasonic imaging typically involves measurements of a single acoustic parameter by transmitting an acoustic signal into a tissue and analyzing the response. For example, reflectivity coefficients may be used to generate reflection images, and attenuation or time-of-flight data may be used to generate transmission images. Sinogram data can be derived from multiple measurements of the acoustic parameter, from which a single-parameter image can be subsequently generated. Such images might be used to visualize a developing baby or circulation of blood, for example.

However, these single-parameter imaging methods are not always sufficient for classifying various types of tissue within an imaged tissue portion. One reason is that such methods typically involve measuring the acoustic parameter, such as attenuation, from peak amplitude values or from total energy of the received. Because ultrasonic signals commonly experience errors of up to 10%, the captured image data often is not sufficiently accurate to classify tissue types accurately. Even time of flight-based imaging has its tissue type classification potential hindered due to frequency-dependent dispersion effects of ultrasonic propagation in tissues that comprise nonlinear inhomogenous propagation medium. There currently are not known methods for accurately classifying portions of a tissue sample according to tissue type through enhancement of a single acoustic parameter of the tissue sample.

INVENTION SUMMARY

The present invention helps solve these and other problems by providing methods and systems for classifying different tissue types through enhancement of a single acoustic trait by extracting multiple aspects therefrom.

In one embodiment, a method for classifying a tissue that is irradiated with an ultrasonic signal includes receiving an interaction signal resulting from the interaction between the ultrasonic signal and at least one portion of the tissue, extracting at least first and second characterizing data from an initial portion of the interaction signal characterizing at least a first and second aspect, respectively, of the initial portion of the interaction signal, the first aspect being different from the second aspect, calculating first and second identification data as a function of the first and second characterizing data, respectively, and matching the first and second identification data to a tissue type by consulting a database containing information correlating identification data associated with at least the first and second aspects to tissue type.

In another embodiment, a method for classifying a tissue that is irradiated with an ultrasonic signal includes receiving an interaction signal resulting from the interaction between the ultrasonic signal and at least one portion of the tissue; performing a Fourier transform on an initial portion of the interaction signal, and calculating a characteristic of the tissue portion as a function of the Fourier transform of the initial portion of the interaction signal.

In a further embodiment, a system for performing a method of classifying a tissue that is irradiated with an ultrasonic signal includes a transmission element for irradiating a portion of the tissue with an ultrasonic signal, a receiver element for subsequently receiving an interaction signal resulting from an interaction between the radiated ultrasonic signal and the tissue portion, and a data storage device for storing a database containing information correlating identification data of first and second tissue aspects with tissue type. The system further includes a processor operatively connected to the receiver element and configured to process the interaction signal and extract at least first and second characterizing data therefrom, the characterizing data characterizing at least a first and second aspect, respectively, of an initial portion of the interaction signal. The processor is further configured to calculate identification data as a function of the characterizing data, the identification data representative of at least first and second aspects of the tissue portion. The processor is operatively connected to the data storage device, and further configured to match the identification data to a tissue type by consulting the tissue type database.

In yet another embodiment, a system for classifying a tissue that is irradiated with an ultrasonic signal includes a transmission element for irradiating a portion of the tissue with an ultrasonic signal and a receiver element for subsequently receiving an interaction signal resulting from an interaction between the radiated ultrasonic signal and the tissue portion. A processor is operatively connected to the receiver element and configured to process the interaction signal and identify the initial portion thereof, perform a Fourier transform on the initial portion of the interaction signal, and calculate a characteristic of the tissue portion as a function of the Fourier transform.

The foregoing and other objects, features, and advantages of the present invention will become apparent from a reading of the following detailed description of exemplary embodiments thereof, in conjunction with the accompanying drawing Figures.

DETAILED DESCRIPTION OF THE PREFERRED EMBODIMENTS

Figure 1:
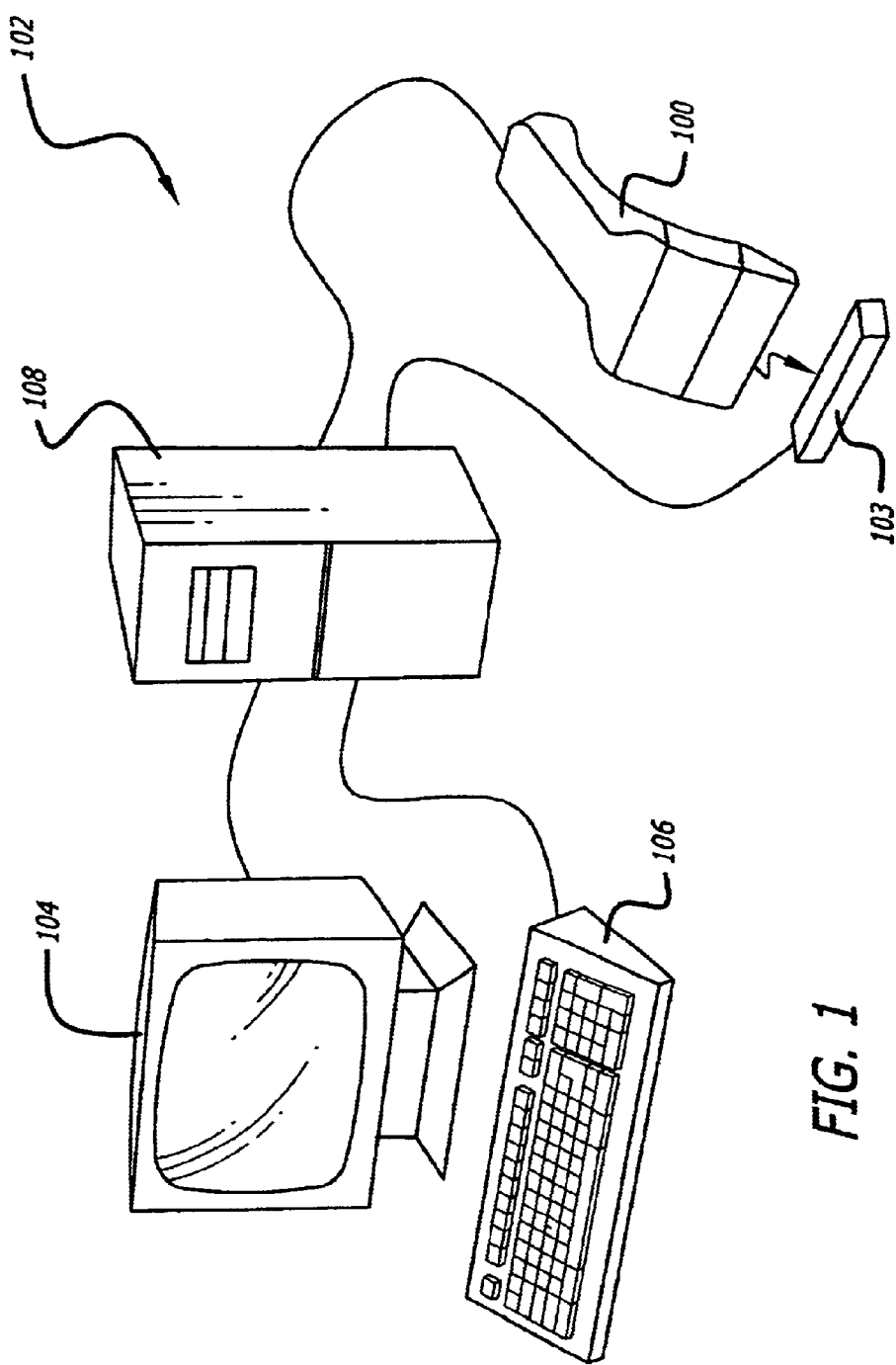
FIG. 1 illustrates an exemplary system for classifying a tissue that is irradiated with an ultrasonic signal.

FIG. 1 illustrates an exemplary system for classifying a tissue that is irradiated with an ultrasonic signal. In the classification process, various portions of the tissue may be differentiated to detect lesions or cancerous portions from normal portions according to differences in characteristics of the tissues. A differentiation technique utilized by the exemplary system analyzes differences in the attenuation characteristics of various types of tissues at different frequencies. A propagating ultrasonic pulse emitted by an ultrasonic imaging system undergoes frequency-dependent attenuation according to the type of material it traverses. Therefore, attenuation or other characteristics of an ultrasonic pulse radiating into a tissue may be measured and processed according to the methods disclosed herein for the purpose of characterizing portions of the tissue to differentiate between various tissue types.

In one embodiment, the system may include a transmission-mode ultrasound machine 102 for emitting an ultrasonic signal into a tissue to be classified, receiving the forward-scattering signal in a modified form as an interaction signal after the emitted ultrasonic signal has interacted with the tissue, and subsequently processing the interaction signal to classify the portion of the tissue it interacted with. A transmitting element 100 or array of transmitting elements may send high-frequency signals, such as 1 to 10 megahertz sound pulses, into the tissue to be tested. The sound waves travel into the tissue and interact therewith, experiencing modifications that may include frequency-dependent signal attenuation. The interaction signal is then received by receiver element 103 or an array of receiver elements, and relayed to ultrasound machine 102 for processing. In an alternative embodiment employing an angle-mode ultrasound machine that measures angle scattering, the propagated signal may scatter within an approximately 60 degree range of transmission or zero degree forward scattering. The angle scattered sound waves may then be received by receiver element 103 and relayed to ultrasound machine 102. Ultrasound machine 102 may also comprise a high resolution ultrasonic transmission tomography (HUTT) system, such as that disclosed in an article entitled "High Resolution Ultrasonic Transmission Tomography" by Marmarelis, et. al., published for *SPIE International Symposium, Medical Imaging* in February, 2003 and incorporated herein by reference. Ultrasound machine 102 may alternatively include echo-mode imaging systems, transmission-mode ultrasound computed tomography (UCT) systems or other imaging systems.

Continuing the description with reference to a transmission-mode system, which includes a transmitting element 100 for transmitting a signal and receiver element 103 for receiving a interaction signal, ultrasound machine 102 may further include a display 104, a user input device 106 and a computer 108. The various components of ultrasound machine 102 may be separate, connectable components as illustrated in FIG. 1, or may be contained within a single device. User input device 106 may be used to provide information to computer 108, such as control information regarding the amplitude, frequency and duration of pulses emitted from transmitting element 100. Computer 108, upon receipt of a transmitted sound wave, which has been altered to become an interaction signal as a result of its interaction with the tissue, may then process that interaction signal to determine information about the tissue. For example, computer 108 may extract attenuation information across multiple frequency bands in the interaction signal, as will be described in further detail below. Other information that may be utilized for tissue classification in an alternative embodiment may include "time of flight," which may be measured as the time it takes each sound wave to travel from transmitting element 100 to receiver element 103, typically on the order of millionths of a second. Display 104 may present an image of the measured acoustic traits of the interaction signal, forming a two dimensional image of the tissue. Display 104 may present additional identification information to supplement the displayed image, indicating tissue type classification. The tissue type classification processing and identification will be described in further detail below.

In an exemplary embodiment, a transmission-mode system may be utilized to perform a tomographic scan that includes azimuthal and angular scans of the tissue using a pair of sub-millimeter transmitting and receiving transducer elements, such as piezoelectric crystals having dimensions of approximately 0.4 mm by 0.4 mm. The transducer elements may be arranged in multi-element transmitter and receiver arrays, and the tomographic scan may be performed in parallel-beam transmission mode, with the system operating at approximately 8 MHz center frequency. Exemplary settings for a tomographic scan may include an azimuthal step of 0.4 mm, a vertical elevation of 0.4 mm and an angular step of 0.5 degrees. Of course, these values are merely illustrative, and it is to be understood that other values that will be readily ascertainable by those skilled in the art are contemplated as being within the scope of the present invention. The tomographic scans produce a plurality of interaction signals that collectively form sinogram data representing a portion of the tissue that is scanned. Depending on the arrangement of the transducer and receiving elements, an interaction signal generated by a scan may represent a single pixel within an image of the tissue portion, a line of pixels, or another multi-pixel configuration.

Figure 2:
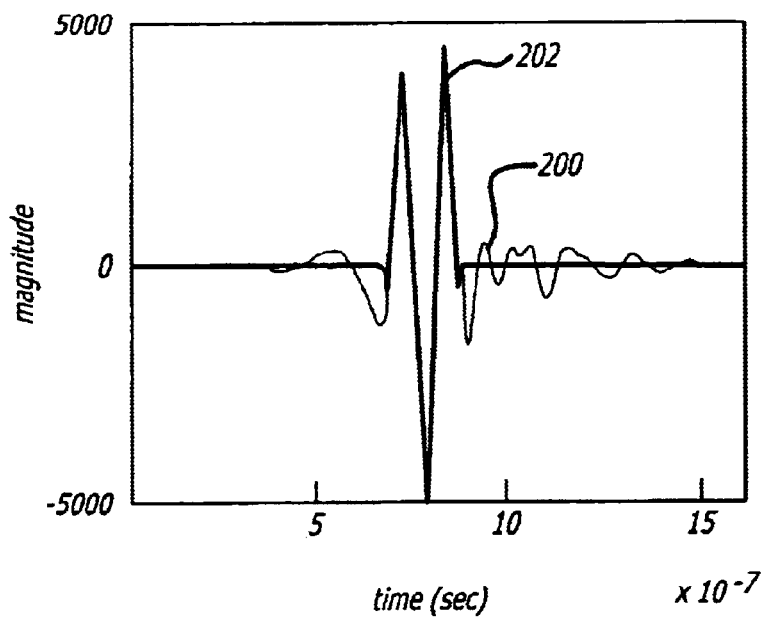
FIG. 2 illustrates an exemplary initial portion of an interaction signal resulting from interaction with a tissue to be classified.

FIG. 2 illustrates an exemplary initial portion of an interaction signal resulting from interaction with a tissue to be classified. In one embodiment, the initial portion of the interaction signal is extracted from the totality of received signals for selective analysis. For example, the first arrival pulse, which does not include contributions from later arriving pulses, may be detected and extracted from the received signal. A plurality of extracted first arrival pulses collectively form sinogram data for a portion of the tissue being scanned. The tissue portion may be represented by a single line within an image, representing a line of pixels, or another pixel configuration depending on the arrangement of the transmitting elements and the configuration of the scan. Regardless of the size of the scanned tissue portion, each extracted first arrival pulse may then be processed to yield a multispectral vector of attenuation values at multiple frequency bands.

In the exemplary embodiment, interaction signal 200 is relayed from a receiving element or receiving array to a processor that will isolate an initial portion of the interaction as the first-arrival pulse of the received interaction signal for analysis. To perform the first-arrival pulse extraction, a filter may be applied to signal 200. The filter may include a threshold determined by the ambient noise level and based on testing and statistical analysis of typical received interaction signals. Then the filter, which may accordingly specify time from left to right, may be applied to signal 200 in order to extract first arrival pulse 202. This process may be repeated such that arrival pulse 202 is extracted at each azimuthal and angular location of a mechanical tomographic scanner in transmission mode. The resultant plurality of first arrival pulses 202 collectively form a two dimensional sinogram of the tissue portion when plotted as azimuthal v. angle components. Each first arrival pulse 202 may then be individually processed to extract a plurality of characterizing data from each. The characterizing data, once extracted, are represented in a domain other than the time domain of the first arrival pulse. The characterizing data of the alternative domain may then establish a third dimension within a three dimensional sinogram. For example, in the case that the pertinent aspect is attenuation at multiple spectral bands, the third dimension of the three dimensional sinogram would be defined by frequency, as extracted through processing the first arrival pulse 202. An exemplary processing algorithm is a discrete Fourier transform, in which the overall spectral width of first arrival pulses 202 is divided into discrete spectral bands. The extraction of characterizing data from the first arrival pulses 202 data may thus from a stack of two dimensional sinograms, with the stack representing a three dimensional sinogram whose third dimension is defined by the spectral bands extracted through the Fourier transform.

Figure 3:
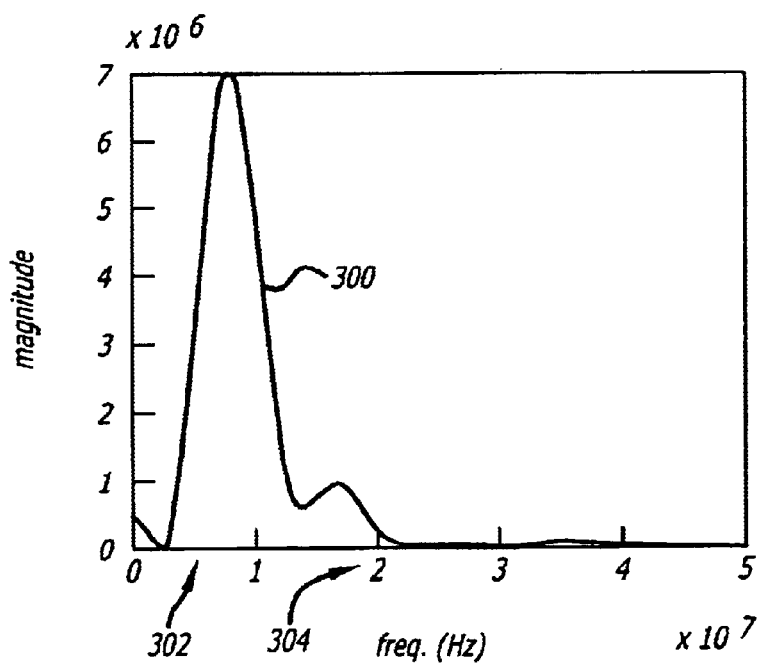
FIG. 3 illustrates a graphical representation of a plurality of characterizing data extracted from an initial portion of an interaction signal.

FIG. 3 illustrates a graphical representation of a plurality of characterizing data 300 extracted from the first portion of an interaction signal. Various types of characterizing data may include attenuation values at multiple frequency bands, phase shifts at multiple frequency bands, time-of-flight values, wavelet decomposition coefficients and the like. Characterizing data 300 may also be extracted through different processing algorithms. For example, a Discrete Fourier Transform on the extracted first arrival pulse may yield discrete values of attenuation at each of a plurality of frequency bands. Characterizing data 300 is thus represented by a curve fit to a plurality of discrete values generated by a Fourier Transform algorithm as applied to an extracted first arrival pulse. The Fourier Transform algorithm may be applied to generate characterizing data for any number of frequency bands. For example, in the case of 20 spectral bands between 5 MHz, represented at point 302, and 20 MHz, represented at point 304, data 300 would comprise discrete values for attenuation at 0.75 MHz intervals. However, it is understood that the number of spectral bands utilized for the processing methods disclosed herein is not limited to 20, and that any multiple number of spectral bands may be used to extract a plurality of characterizing data from a first arrival pulse in accordance with the teachings of the present invention. Also, characterizing data may be generated by normalizing the Fourier transform with the Fourier transform of an interaction signal generated by transmitting an ultrasonic signal through water. That is, the Fourier transform from which characterizing data are extracted may comprise a ratio of the Fourier transform of a tissue-based interaction signal to the Fourier transform of a water-based interaction signal.

Once extracted from an interaction signal, a plurality of one type of characterizing data may define a multi-characteristic vector. The multi-component vector represents attenuation at multiple frequency bands in a single pixel of an image representing the tissue. In turn, a plurality of vectors may form a three dimensional sinogram representing a three-dimensional image of the received interaction signal. The three dimensional sinogram represents a line of pixels within the image, measured by the transducer at a given angle in the imaging plane at varying distances along the detector array. The intensity of the pixels represents attenuation of the signal caused by interaction with the tissue portion it passed into. The frequency-dependent attenuation can be obtained as the ratio of the frequency spectrum of the signal entering each tissue portion represented in a resultant image by a single pixel, to the spectrum of the forward-scattered interaction signal. Therefore, the received interaction signal comprises a modified ultrasonic wave traversing a line of pixel-represented tissue portions and thus represents a single line within an image of the tissue portion.

After performing a Fourier Transform on each interaction signal to extract multi band characterizing data as described above, image reconstruction is accomplished by applying filtered back-projection algorithms to the data in each of the extracted spectral bands. Applicable filtered back-projection algorithms for image reconstruction will be readily apparent to those skilled in the art. Applying the filtered back-projection algorithms to each of the two-dimensional sinograms that are components of the three-dimensional sinogram achieved by the Fourier Transforms above results in a stack of images representing a three dimensional multi-band augmentation of a two dimensional tomographic slice, wherein the third dimension is represented by the plurality of spectral bands extracted through the Fourier Transform. Thus, the multispectral image representation contains multi-band identification data of individual pixels that can be used for tissue classification of the tissue portions, such that tissue portions may be distinguished according to various tissue types. Isolation of multi-band identification data of individual pixels from a three dimensional image may, in some embodiments, include spectral unmixing techniques as described in an article titled "Multi-band Tissue Differentiation in Ultrasonic Transmission Tomography" by Marmarelis et. al., published for *SPIE International Symposium, Medical Imaging* in February 2003, incorporated herein by reference.

Figure 4:
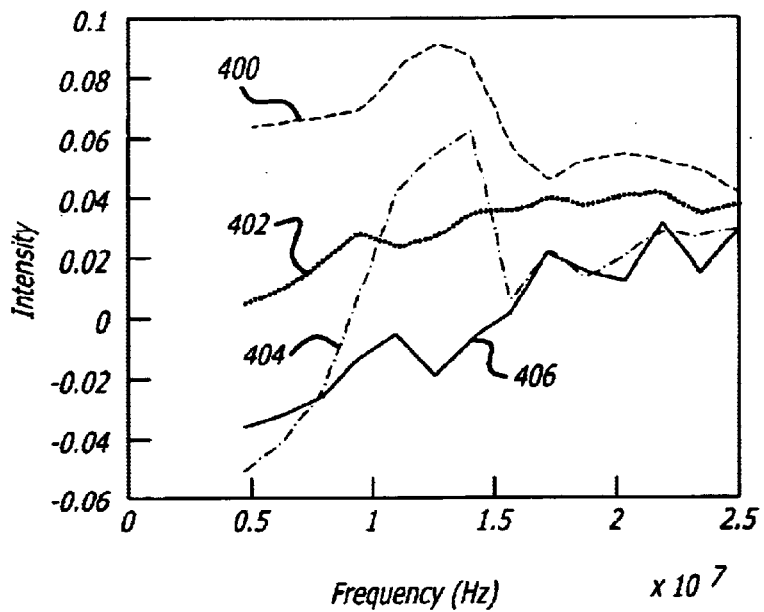
FIG. 4 illustrates a graphical representation of tissue type characteristics.

FIG. 4 illustrates a graphical representation of known tissue type characteristics. After the multi-band characteristics of individual pixels are isolated, the resultant multi-characteristic vector may be compared to the known tissue type characteristics. Each data set 400, 402, 404 and 406 represents a multi-characteristic vector of a different tissue type, identified through laboratory testing. For example, in breast imaging applications, tissue types for which known multi-characteristic vectors would be stored in a database for comparison with tested breast tissue portions may include normal tissue, fat, blood vessels, mammary ducts, benign lesions, malignant lesions, microcalcifications, lobules, cysts, and other tissue types. Known multi-characteristic vectors for each of the various tissue types may be developed in accordance with the methods described above and stored in a database for comparison with extracted multi-characteristic vectors of unknown tissue portions to classify them as to tissue type. For example, characterizing data may be processed and determined for a tissue portion of unknown tissue type, then compared with a multi-characteristic vector database containing information correlating characterizing data of multiple aspects with tissue type. In the case of multiple aspects comprising attenuation in multiple frequency bands, known multi-characteristic vectors represented by data sets 400, 402, 404 and 406 represent the known attenuation at certain frequency bands in each of a different type of tissue. Then, a tissue portion of unknown tissue type may be analyzed according to the methods described above, and have a multi-characteristic vector constructed according to its measured and analyzed attenuation at the same frequency bands as those included in data sets 400, 402, 404 and 406. Finally, the multi-characteristic vector of the tissue portion of unknown tissue type may be compared to the multi-characteristic vectors represented by stored data sets 400, 402, 404 and 406, wherein a substantial match is indicative of the tissue type of the analyzed tissue portion.

Figure 5:
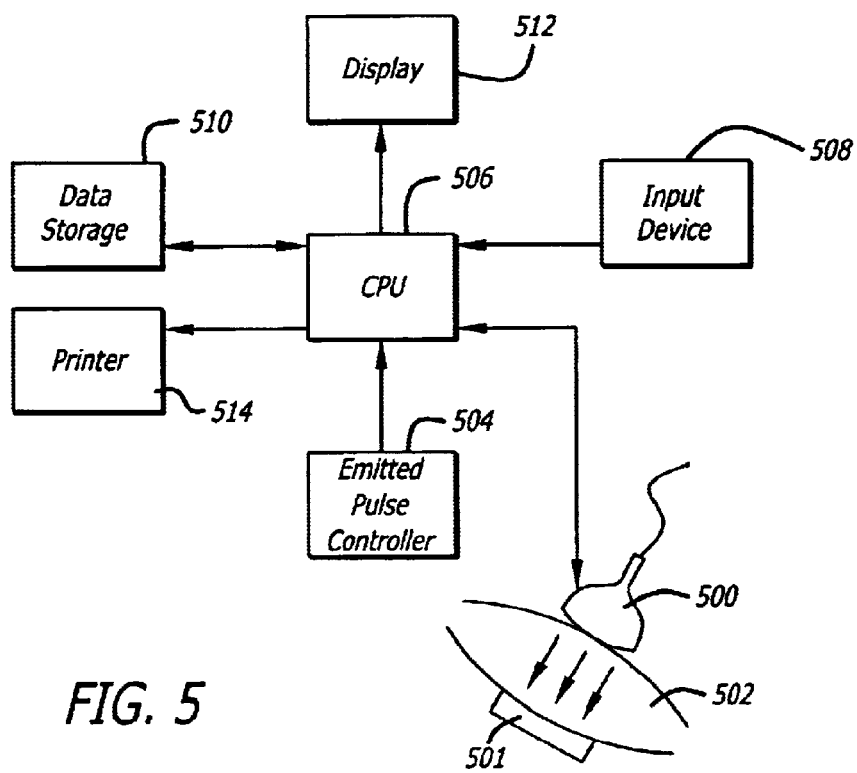
FIG. 5 is a block diagram of various components within an exemplary system for classifying a tissue that is irradiated with an ultrasonic signal.

FIG. 5 is a block diagram of various components within an exemplary system for classifying a tissue that is irradiated with an ultrasonic signal. Emitter array 500 irradiates tissue 502 with an ultrasonic signal. Various characteristics of the ultrasonic signal may be controlled by a user through emitted pulse controller 504, which is operatively connected to a central processing unit (CPU) 506. CPU 506 may also receive other user input through a user input device 508 such as a keyboard, mouse, tracking ball, or other similar device. An interaction signal, changed as a result of interaction with tissue 502, is received by emitter array 500 and relayed to CPU 506 where it is processed and analyzed as described above. Data storage 510 may contain multi-characteristic vectors of known tissue types for comparison with an analyzed multi-characteristic vector of tissue 502, to distinguish between various tissue types of tissue portions therein. The classification of various portions of tissue 502 may be reported to a user in various ways including imaging on a display 512. The tissue 502 may be represented in an image, with its classified tissue portions represented by varying colors or shades according to tissue type. Alternatively, various tissue types may be reported to a user by printing characterizing data of tissue portions through printer 514. Of course, other reporting methods are possible as well.

While the specification describes particular embodiments of the present invention, those of ordinary skill can devise variations of the present invention without departing from the inventive concept. The foregoing description of particular embodiments of the invention has been presented for the purposes of illustration and description. It is not intended to be exhaustive or to limit the invention to the preceise form disclosed. Many modifications and variations are possible in light of the above teaching. For example, the extraction of multi-aspect characterizing data from a portion of sinogram data, such as by performing a Fourier Transform, may be performed on an individual pixel rather than on a line of pixels represented by the sinogram data portion. Also, other extraction algorithms may be utilized instead of the Fourier Transform. For example, wavelet decomposition, principal component analysis, independent component analysis and other types of signal decomposition known in the art may be performed to extract multi-aspect characterizing data from the sinogram data. Moreover, multi-aspect characterizing data is not limited to data representing multiple spectral bands; rather, it may include other components of the sinogram data such as phase shift components that may be extracted with Fourier Transforms, decomposition, or other processing algorithms. Further, multi-characteristic vectors representing the multi-characteristic data of a tissue portion may include time of flight or other information.

I claim:

1. A tissue classifying system comprising:

an ultrasonic transmitting system configured to transmit a plurality of pulses through the tissue at various angles with respect to the tissue;

an ultrasonic receiving system oriented opposite of the transmitting system such that:
the tissue may be positioned between the transmitting system and the oppositely-oriented receiving system; and
the receiving system receives each pulse that is transmitted by the transmitting system after it propagates through and is forward scattered by the tissue;

a database configured to store frequency-dependent transmission characteristics about various types of tissue; and a processing system configured to be in communication with the transmitting system, the receiving system and the database and configured to:

deliver ultrasonic pulses to the transmitting system;
receive ultrasonic signals from the receiving system, each ultrasonic signal including a representation of an ultrasonic pulse that is transmitted by the transmitting system after the pulse propagates through and is forward scattered by the tissue;
extract an initial portion from each received signal;
perform a Fourier decomposition on the extracted initial portion of each received signal;
determine frequency-dependent transmission characteristics of a pixel within the tissue based on the Fourier decomposition of the extracted initial portion of the received signals; and
determine the tissue type of the pixel based on a comparison of the frequency-dependent transmission characteristics of the pixel with the information in the database.

2. The tissue classifying system of claim 1 wherein:
the transmitting system includes an array of ultrasonic transmitting elements, each configured to transmit a pulse through the tissue at an azimuthal location that is different from the azimuthal location of the other transmitting elements; and
the receiving system includes an array of ultrasonic receiving elements, each oriented opposite of one of the transmitting elements such that:
the tissue may be positioned between the receiving element and the one of the transmitting elements; and
the receiving element receives each pulse that is transmitted by the one of the transmitting elements after it propagates through and is forward scattered by the tissue.

3. The tissue classifying system of claim 1 wherein:
the Fourier decomposition on the extracted initial portion of each received signal includes Fourier components;
the frequency-dependent transmission characteristics of the pixel are expressed in the form of a vector based on the Fourier components; and
the determine the tissue type includes comparing the vector with the information in the database.

4. The tissue classifying system of claim 1 wherein the processing system is configured to normalize the Fourier decomposition of each extracted initial portion based on a Fourier decomposition of an initial portion of an ultrasonic pulse that have passed from the transmitting system to the receiving system with no tissue in between.

5. The tissue classifying system of claim 1 wherein each initial portion consists of the first forward scattered arrival of the pulse that is transmitted by the ultrasonic transmitting system and does not contain any later arrival of that pulse.

6. The tissue classifying system of claim 1 wherein the frequency-dependent transmission characteristics of the pixel includes frequency-dependent transmission attenuation information and wherein the comparison compares the frequency-dependent transmission attenuation information.

7. The tissue classifying system of claim 1 wherein the frequency-dependent transmission characteristics of the pixel includes frequency-dependent transmission phase information and wherein the comparison compares the frequency-dependent transmission phase information.

8. The tissue classifying system of claim 7 wherein the frequency-dependent transmission characteristics of the pixel includes frequency-dependent transmission attenuation information and wherein the comparison compares the frequency-dependent transmission attenuation information.

* * * * *